United States Patent [19]

Hodgen

[11] Patent Number: 5,622,943
[45] Date of Patent: Apr. 22, 1997

[54] MINIMIZING PROGESTIN ASSOCIATED BREAKTHROUGH BLEEDING

[75] Inventor: Gary D. Hodgen, Norfolk, Va.

[73] Assignee: The Medical College of Hampton Roads, Norfolk, Va.

[21] Appl. No.: 331,606

[22] PCT Filed: May 3, 1993

[86] PCT No.: PCT/US93/04003

§ 371 Date: Dec. 6, 1994

§ 102(e) Date: Dec. 6, 1994

[87] PCT Pub. No.: WO93/21927

PCT Pub. Date: Nov. 11, 1993

[30] Foreign Application Priority Data

May 6, 1992 [WO] WIPO ............... PCT/US92/03574

[51] Int. Cl.$^6$ .................................................. A61A 31/56
[52] U.S. Cl. .......................................... 514/179; 514/843
[58] Field of Search ................................... 514/179, 843

[56] References Cited

PUBLICATIONS

Chem. Abst. 115(11):106339a Batista, et al. 1991
Drug Facts and Comparisons, 1996 pp. 108–108.

*Primary Examiner*—John W. Rollins
*Attorney, Agent, or Firm*—Sughrue, Mion, Zinn, Macpeak & Seas

[57] ABSTRACT

A method for minimizing menstrual bleeding irregularities in individuals using progestin-only pharmaceutical preparations, such as contraceptives, is disclosed.

21 Claims, 2 Drawing Sheets

MINIMIZING PROGESTIN ASSOCIATED BREAKTHROUGH BLEEDING

FIELD OF THE INVENTION

The invention relates to compositions and methods for minimizing breakthrough bleeding in users of progestin-only pharmaceutic preparations, such as contraceptives.

BACKGROUND OF THE INVENTION

The primate menstrual cycle is characterized by a proliferation and regression of the uterine lining under the control of steroid hormones, primarily estrogen and progesterone. It is believed that the staggered cyclic levels of hormones contribute to the growth and shedding of the upper tissue compartment of the uterus.

The endometrium on the uterus is characterized by distinct layers, such as the stratum functionalis and stratum basalis. It is the functionalis which represents the transient upper tissue compartment that is shed during menstruation.

It is believed that the basalis serves as a source of new cells for the regeneration of the functionalis in succeeding cycles. Wilborn & Flowers, Seminars in Reproductive Endocrinology 2:4, 307, 1984; Padykula et al., Biology of Reproduction 40, 681, 1989. If the basalis does serve as a germinal layer, then the effects of damage to the basalis during a given cycle could be manifest in succeeding cycles.

Because endometrial proliferation serves to prepare the uterus for an impending pregnancy, manipulation of hormones and of the uterine environment can serve as suitable targets for contraception. For example, estrogens are known to decrease follicle stimulating hormone secretion by feedback inhibition.

Under certain circumstances, estrogens can also inhibit luteinizing hormone secretion, once again by negative feedback, although under normal circumstances it is believed that the spike of circulating estrogen found just prior to ovulation induces the surge of gonadotrophin hormones that occurs just prior to and resulting in ovulation. High doses of estrogen also can prevent conception probably due to interference with implantation.

Progesterone is responsible for the progestational changes of the endometrium and the cyclic changes of cells and tissues in the cervix and the vagina. For example, progesterone makes the cervical mucus thick, tenacious and cellular. It is believed that thickened mucus impedes spermatozoal transport.

Progesterone has somewhat of an anti-estrogenic effect on the myometrial cells, for example, decreasing the excitability of the smooth muscle cells, and the like. It is known that large doses of progesterone inhibit luteinizing hormone secretion and progesterone injections can prevent ovulation in humans.

The most prevalent form of oral contraception is a pill that combines both an estrogen and a progestagen, the so-called combined oral contraceptive preparations. Apparently, the estrogen and progestagen act in concert to block gonadotrophin release.

Alternatively, there are oral contraceptive preparations that comprise a progestagen only. Such preparations are indicated particularly for individuals who have experienced side effects or an intolerance to the combined preparations or in lactating women because of the lack of an estrogenic effect on lactation.

However, the progestagen-only preparations have a more varied spectrum of side effects than do the combined preparations. A disadvantage of the progestagen-only preparations is the relatively high incidence of bleeding problems, such as, prevalent or heavier menstrual spotting, amenorrhea and more breakthrough bleeding. Thus, the combined preparations are the preferred oral contraceptives in use today. Sheth et al., Contraception 25,243, 1982.

Some of the very common side effects of the progestagen-only oral contraceptives is the increased incidence of menstrual spotting, break. through bleeding, variations in menstrual cycle length and occasionally amenorrhea.

Nevertheless, it would be preferable to have an contraceptive preparation that minimizes the amounts of estrogens and progestagens used. For example, estrogens are known to cause dizziness, nausea, headache and breast tenderness. Thus, a progestagen-only contraceptive would forego such possible problems and be an improvement over the combined preparations if the above-referred to problems of progestagen-only contraceptives also can be remedied. George Washington University Medical Center, Population Reports, Series A, No. 3, September 1975.

Anti-progestins include inhibitors of progesterone synthesis, ligands, such as antibodies, to progesterone and progesterone receptor antagonists. For example, mifepristone (RU486) is a progesterone receptor antagonist. RU486 binds to the progesterone receptor and produces antagonistic effects. Following oral administration, RU486 in the human has a half life of about 20–24 hours. When administered in the luteal phase of the menstrual cycle, RU486 induces luteolysis and vaginal bleeding.

RU486 may act directly on the endometrium to induce vaginal bleeding. RU486-mediated luteolysis appears to be secondary to changes in gonadotrophin secretion and thus the effects are similar to those following exogenous progesterone administration. Baulieu, Science 245, 1351, 1989.

Swahn et al. (Human Reproduction 5(4), 402, 1990) relates to administering RU486 early during the luteal phase prior to implantation. Those authors found that a single dose of RU486 administered on the second day after the LH peak causes a retardation of endometrial development, without upsetting the menstrual cycle. Those authors speculated that it may be possible that the effect on the endometrium may be sufficient to prevent implantation.

SUMMARY OF THE INVENTION

It is an object of the instant invention to provide a method and means of enhancing the value progestin-only pharmaceutical preparations, such as contraceptives.

It is another object of the instant invention to provide a kit and/or program to enhance the every day use of progestin-only pharmaceutical preparations, such as contraceptives.

Those and other objects have been achieved in the development of a method for minimizing uterine bleeding in a female using a progestin-only pharmaceutical preparation comprising administering to said female a biologically effective amount of an anti-progestin.

The invention also relates to a method of birth control comprising administering to a female a composition comprising biologically effective amounts of a progestin and an anti-progestin.

Further, the invention relates to a contraceptive composition comprising a progestin and an anti-progestin.

The invention also relates to an implant intended for subcutaneous or local administration comprising a pharmaceutically acceptable inert core material which would function as a matrix, a progestin and an anti-progestin.

The invention further relates to a kit. comprising a plurality of pills or tablets to be administered sequentially at one per day, wherein said pills or tablets are placebos except for an active agent-containing pill or tablet comprising an anti-progestin.

DETAILED DESCRIPTION OF THE INVENTION

Figure 1:
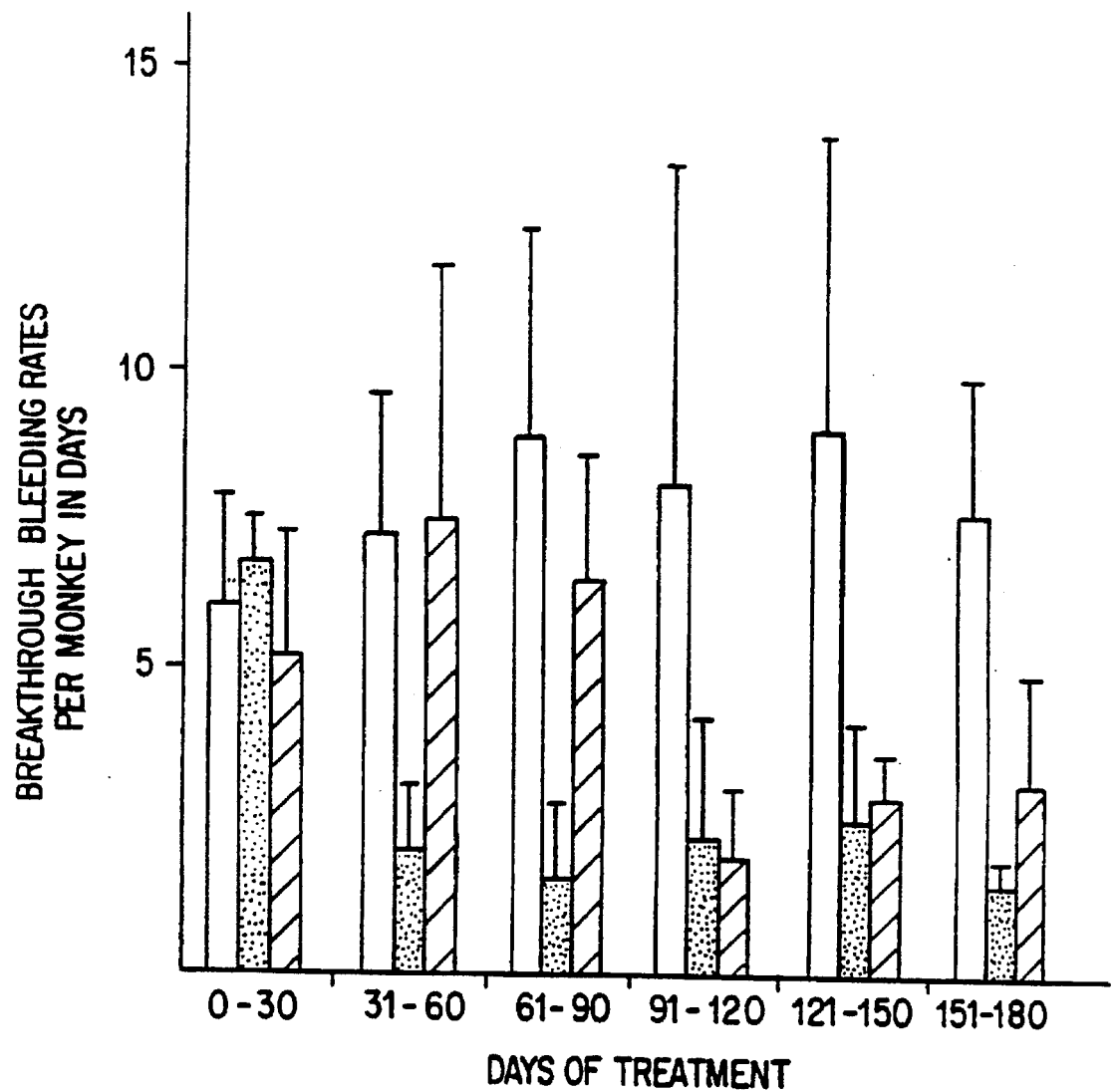
FIG. 1 depicts the breakthrough bleeding rate per monkey over the course of treatment. Individual monkeys were given a progestin-only contraceptive and intermittent dosing of anti-progestin. Breakthrough bleeding was scored on all days except for the seven days following an RU486 dose. The average duration of bleeding following an RU486.dose was 3.2±1.1 days. The incidence of RU486-induced menses was 100% within 72 hours. Open bars indicate monkeys receiving oral contraceptive, levonorgestrel, only. Stippled bars represent monkeys receiving levonorgestrel and RU486 at days 30, 60, 90, 120, 150 and 180. Cross-hatched bars indicate monkeys receiving levonorgestrel and RU486 at days 90 and 180. The daily dose of levonorgestrel was 10 μg per day orally except on the day when RU486 was given when no progestin was administered. RU486 was administered orally and intermittently at 50 mg per dose.

The instant invention relates to a method and means for reducing irregular bleeding in those users of progestagen-only pharmaceutical preparations, such as contraceptives. The invention relates to the use of an anti-progestin in combination with the progestagen-only pharmaceutical preparations, such as a contraceptive. For the purposes of the instant invention, progestin and progestagen are considered synonyms.

Progestagen-only pharmaceutical preparations, such as tablets which can be administered orally, vaginal rings, implant systems (biodegradable or not), injectables and transdermal systems, which can be used as contraceptives are known in the art.

For example, commonly used oral contraceptives contain the synthetic progestins, cingestol, ethynodiol diacetate, lynestrenol, norethindrone, norgestrel, quingestanol acetate, levonorgestrel (active ingredient of NORPLANT), norethisterone, chlormadinone, megestrol, desogestrel, gestodene, norgestimate and the like. Fotherby, Journal of Drug Development 4 (2), 101, 1991. Essentially any progestin suitable for use in a progestagen-only pharmaceutical can be used in the practice of the instant invention.

The anti-progestin can be an inhibitor of progesterone synthesis, such as epostane, azastene or trilostane (Creange, Contraception 24, 289, 1981; Drugs of the Future 7, 661, 1982; van der Spuy et al., Clin. Endo. 19, 521, 1983; Birgerson et al., Contraception 35, 111, 1987; U.S. Pat. No. 3,296,255) or a progesterone receptor antagonist, or any such pharmaceutically suitable agent that counteracts the normal biological activity of progesterone, such as antibodies or ligands bindable to progestins or to the progesterone receptor.

A suitable anti-progestin is a progesterone receptor antagonist. For example, RU486, Onapristone, Org 31710 ((6α,11β,17β)-11-(4-dimethylaminophenyl)-6-methyl-4', 5,'-dihyrospiro[estra-4,9-diene-17,2'(3'H)-furan]-3-one), Org 33628 ((11β,17α)-11-(4-acetylphenyl)-17,23-epoxy-19,24-dinorchola-4,9,20-trien-3-one) and Org 31806 ( (7β, 11β,17β)-11-(4-dimethylaminophenyl-7-methyl-4', 5'-dihydrospiro[estra-4,9-diene-17,2'(3'H)-furan]-3one) are particularly suitable in the practice of the instant invention. U.S. Pat. No. 4386085.

The anti-progestin can be administered by way of any art-recognized means practiced in the pharmaceutic arts. For example, a suitable anti-progestin may be so formulated so that it can be administered orally, via a skin patch for transdermal absorption, contained within an inert matrix which is implanted within the body and in the implanted state is released slowly, such an implant is taught in U.S. Pat. Nos. 4,957,119 and 5,088,505 and the like.

Thus, pharmaceutic formulations of solid dosage forms include tablets, capsules, cachets, pellets, pills, powders or granules; topical dosage forms include solutions, powders, fluid emulsions, fluid suspensions, semi-solids, ointments, pastes, creams, gels or jellies and foams; and parenteral dosage forms includes solutions, suspensions, emulsions or a dry powder comprising an effective amount of anti-progestin as taught in the instant invention.

It is known in the art that the active ingredient, the anti-progestin, can be contained in such formulations in addition to pharmaceutically acceptable diluents, fillers, disintegrates, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance, see, for example, "Modern Pharmaceutics" Banker & Rhodes, Marcel Dekker, Inc. 1979; "Goodman & Gilman's The Pharmaceutical Basis of Therapeutics", 6th Edition, MacMillan Publishing Co., New York 1980.

In the case of oral contraceptives, it is known that the kits thereof contain a pill for each day of the month (either 28 days, the lunar month, or 30 days) wherein any one pill may be a placebo or may contain one or more of the active ingredients.

The effective amount of an anti-progestin in the practice of the instant invention can be determined using art-recognized methods, for example, by establishing dose-response curves in suitable animal models and extrapolating therefrom to humans, extrapolating from suitable in vitro systems or by determining effectiveness in clinical trials. The determination of an effective dose is a routine exercise in the pharmaceutic arts. The artisan will take into account various physical parameters of the prospective host such as weight, age and the like.

In like vein, the dosage regimen of the preparation is determinable using art-recognized methods such as establishing a dose response curve in similar primate models or in a suitable in vitro experimental system or by an empirical determination in clinical trials.

It is contemplated, in view of the dynamic state of the endocrine system in primates, that administration of the anti-progestin can be either on a tonic or continuous basis, such as in parallel with administration of a progestin-only oral contraceptive, or on an episodic basis because of the dynamic relationship of the endometrial cells and the long term effects of anti-progestins. Thus, the anti-progestin can be administered in combination with the progestin in the form of a pill or as a co-component in an implant or the progestin can be given in one form and the anti-progestin can be given in another form, for example, the progestin may be given in the form of a pill and the anti-progestin can be delivered as a component of an implant. Alternatively, the progestin can be administered daily whereas the anti-progestin is administered monthly, or at other intermittent intervals.

In the case of the progesterone receptor antagonists RU486, Org 33628, Org 31806 and Org 31710, it is anticipated that a suitable human oral dose will be on the order of 10–250 mg per dose. The amount per dose can be lowered or raised based on the number of doses actually given, that is the interval at which the doses of anti-progestin are administered and characteristics of the individual receiving the treatment and the potency of a particular anti-progestin.

The number of doses can vary from monthly to longer intervals taking into consideration cost, safety and the like. Thus, a suitable regimen is having the anti-progestin administered every thirty days, every sixty days or every ninety days. Alternatively, in the case of contraceptives where many of the pill kits are configured based on the lunar month, the anti-progestin can be administered on the twenty-eighth day of each cycle. Variations of dosage based on route of administration may vary and such changes can be determined practicing known techniques as described above.

All references cited herein are herein incorporated by reference.

The present invention is described further below with respect to specific examples which are tended to illustrate the instant invention without limiting the scope thereof.

EXAMPLE

In the present study, laboratory primates (Macaca fascicularis, n=18), having normal ovulatory menstrual cycles, were assigned at random to one of three groups: Group I (n=6) received 10 µg of levonorgestrel daily by oral ingestion for 180 days. Group II (n=6) was given the same dose regimen of levonorgestrel as in Group I, except that 50 mg of RU486 was administered orally and intermittently on treatment days 30, 60, 90, 120, 150 and 180. Similarly, Group III primates (n=6) received levonorgestrel daily, but RU486 on treatment days 90 and 180. For Groups II and III, levonorgestrel was withheld only on the days that the anti-progestin was given.

Breakthrough bleeding was recorded daily based on presence or absence of blood in the vagina upon insertion of a saline-moistened cotton-tipped applicator. Menstrual bleeding that occurred within 7 days after each RU486 treatment was not counted as breakthrough bleeding.

To determine whether the dose of levonorgestrel reliably blocked ovulation, all primates were bled daily from the femoral vein (3.0 ml) from treatment day 91 to 120, so that serum estradiol and progesterone levels could be determined by radioimmunoassay using known materials and techniques.

Intermittent RU486 treatment in animals receiving a progestin daily markedly reduced irregular menstrual bleeding by 69% on average, whether the interval between treatments of the anti-progestin was 30 or 90 days (p<0.05). However, there was a trend (p>0.05) toward rising breakthrough bleeding in the 2nd and especially 3rd month after RU486 treatment (Group III).

That the daily dose regimen of levonorgestrel effectively blocked ovulation was evident from the absence of overt serum progesterone elevations. The intermittent doses of anti-progestin did suppress transiently mean tonic serum estradiol to below 30 pg/ml for four or five days; otherwise ovarian estrogen secretion was non-episodic (48±11 pg/ml, Group I; 41±6 pg/ml, Group II; and 42±9 pg/ml; Group III).

More importantly, intermittent administration of RU486 significantly reduced irregular menstrual bleeding whether the every 30 day or every 90 day anti-progestin regimen was employed, albeit the anti-progestin impact appeared to fade with less frequent dosing.

The bleeding control effect of RU486 was manifest for two to three months. The anti-progestin may have imparted certain long-lasting functional characteristics in basal endometrial cells. The primate data show the effectiveness of combining progestin with an anti-progestin, without the need for exogenous estrogen, to control endometrial bleeding.

Figure 2:
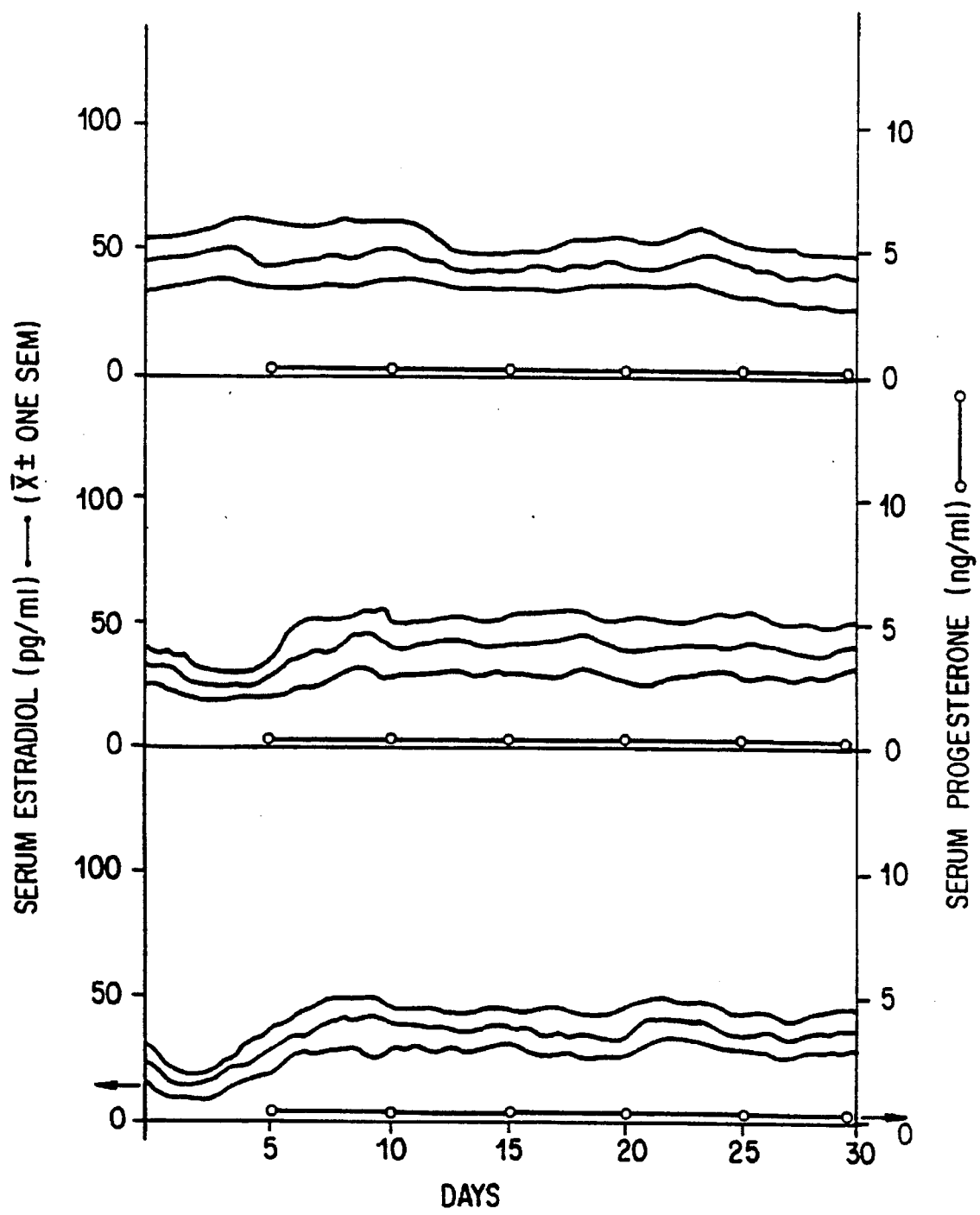
FIG. 2 depicts serum estradiol and progesterone levels in monkeys of the various treatment groups. The lower limit of detection of estradiol was 12 pg/ml. The lower limit of detection of progesterone was 0.2 ng/ml. The top panel depicts animals receiving progestin only on a daily basis. The middle panel depicts animals receiving progestin daily and RU486 on days 30, 60, 90 and 120. The bottom panel depicts animals receiving progestin daily and RU486 on day 90 only. The progestin was levonorgestrel.

It should be noted that the efficacy of the progestin to block ovulation is not compromised by the intermittent administration of an anti-progestin. See FIG. 2.

While the invention has been described in detail and with reference to certain embodiments thereof, it would be apparent to one skilled in the art that various changes and modifications can be made without departing from the spirit and scope thereof.

What is claimed:

1. A method for minimizing uterine bleeding in a female using a progestin-only pharmaceutical preparation comprising administering to said female a biologically effective amount of an anti-progestin.

2. The method of claim 1, wherein said anti-progestin is a compound that inhibits progesterone synthesis or is a progesterone receptor antagonist.

3. The method of claim 2, wherein said antagonist is selected from the group consisting RU486, Org 33628, Org 31806 and Org 31710.

4. The method of claim 3, wherein said antagonist is administered in a dose of about 10 mg to about 250 mg per dose.

5. The method of claim 3, wherein said antagonist is administered once every 30 days.

6. The method of claim 3, wherein said antagonist is administered once every 60 days.

7. The method of claim 3, wherein said antagonist is administered once every 90 days.

8. The method of claim 3, wherein said antagonist is administered on the 28th day of a cycle.

9. The method of claim 1, wherein said progestin is desogestrel.

10. The method of claim 1, wherein said progestin and said anti-progestin are administered concurrently.

11. The method of claim 1, wherein said anti-progestin is administered in the form of a pill or tablet.

12. The method of claim 1, wherein said anti-progestin is administered as a component of an implant.

13. A method of minimizing breakthrough bleeding associated with a progestin-only birth control method comprising administering to a female a composition comprising an amount of a progestin suitable for contraception and an anti-progestin in an amount which minimizes breakthrough bleeding.

14. A progestin-only contraceptive composition with minimal breakthrough bleeding comprising a progestin and an anti-progestin in an amount which minimizes breakthrough bleeding.

15. The composition of claim 14, wherein said progestin is desogestrel.

16. The composition of claim 14, wherein said anti-progestin is selected from the group consisting of RU486, Org 33628, Org 31710 and Org 31806.

17. The composition of claim 14, wherein said progestin is desogestrel and said anti-progestin is Org 31710.

18. A progestin-only contraceptive implant intended for subcutaneous or local administration with minimal breakthrough bleeding comprising a pharmaceutically acceptable inert core material which would function as a matrix, a progestin and an anti-progestin in an amount which minimizes breakthrough bleeding.

19. A progestin-only contraceptive kit comprising a plurality of pills or tablets to be administered sequentially at one per day, wherein said pills or tablets are placebos or contain a progestin except for an active agent-containing pill or tablet comprising an anti-progestin in an amount which minimizes breakthrough bleeding.

20. The kit of claim 19, wherein said kit comprises at least 28 pills or tablets and said active agent-containing pill or tablet is administered on the 28th day.

21. The kit of claim 19, wherein said kit comprises at least 30 pills or tablets and said active agent-containing pill or tablet is administered on the 30th day.

* * * * *